(12) United States Patent
Larson (10) Patent No.: US 11,148,260 B2
(45) Date of Patent: Oct. 19, 2021

(54) TORQUE-ANGLE STRUCTURAL FASTENING SYSTEM

(76) Inventor: Chad M. Larson, Savage, MN (US)

( * ) Notice: Subject to any disclaimer, the term of this patent is extended or adjusted under 35 U.S.C. 154(b) by 1572 days.

(21) Appl. No.: 14/004,618

(22) PCT Filed: Mar. 20, 2012

(86) PCT No.: PCT/US2012/029773
§ 371 (c)(1),
(2), (4) Date: Nov. 6, 2013

(87) PCT Pub. No.: WO2012/129212
PCT Pub. Date: Sep. 27, 2012

(65) Prior Publication Data
US 2014/0048299 A1 Feb. 20, 2014

Related U.S. Application Data

(60) Provisional application No. 61/466,431, filed on Mar. 22, 2011.

(51) Int. Cl.
*B25B 13/48* (2006.01)
*B25B 21/00* (2006.01)
(Continued)

(52) U.S. Cl.
CPC ............ *B25B 13/48* (2013.01); *A61C 8/0092* (2013.01); *A61L 27/18* (2013.01); *A61L 27/56* (2013.01); *B25B 21/008* (2013.01); *B25B 23/14* (2013.01)

(58) Field of Classification Search
None
See application file for complete search history.

(56) References Cited

U.S. PATENT DOCUMENTS 2,531,048 A 11/1950 Huck
2,928,302 A 3/1960 Owen et al.
(Continued)

FOREIGN PATENT DOCUMENTS

DE 10302707 A1 9/2003
DE 20 2007 013 473 U1 12/2007
(Continued)

OTHER PUBLICATIONS

HSSA, High Strength Squirter Assemblies (8 pages) printed from website of Cooper & Turner Limited (www.cooperandturner.co.uk), Construction, Railway and General Engineering Fastenings; Oct. 2002 and May 2003.
(Continued)

*Primary Examiner* — Hemant Desai
*Assistant Examiner* — Tanzim Imam
(74) *Attorney, Agent, or Firm* — Stradley Ronon Stevens and Young LLP (57) ABSTRACT

A fastening system that comprises a fastener and a single tool that provides both snugging torque and final tensioning to the fastener assembly, from a single side, with a single operator, with no torque feedback. The fastener comprises a nut and a bolt with a head and a shank extending axially from the head. The shank has at least one threaded portion and at least one splined portion, the splined portion defining the end of the bolt. The splined portion remains connected to the threaded portion after final tensioning. The tool comprises a first socket and a second socket, wherein the first socket is engaged with an outer surface of the nut and the second socket is engaged with the splined portion on the fastener. Snugging torque and final tension are both controlled by the tool.

20 Claims, 3 Drawing Sheets

(51) Int. Cl.
   *B25B 23/14*   (2006.01)
   *A61C 8/00*    (2006.01)
   *A61L 27/18*   (2006.01)
   *A61L 27/56*   (2006.01)

(56) References Cited

U.S. PATENT DOCUMENTS

| | | | |
|---|---|---|---|
| 3,057,246 A | | 10/1962 | Brilmyer |
| 3,318,390 A | * | 5/1967 | Hoza .................. B25B 23/1453 173/178 |
| 3,915,053 A | | 10/1975 | Ruhl |
| 4,503,736 A | * | 3/1985 | Fushiya ................ B25B 21/001 81/55 |
| 4,637,764 A | | 1/1987 | Imai |
| 4,659,267 A | | 4/1987 | Uno et al. |
| 4,836,063 A | | 6/1989 | Fushiya |
| 4,845,998 A | * | 7/1989 | DeMartelaere ......... B25B 23/14 73/761 |
| 4,943,196 A | | 7/1990 | Dahl |
| 4,987,669 A | * | 1/1991 | Makimae ................ B25B 23/14 29/407.03 |
| 5,049,016 A | | 9/1991 | Nordyke |
| 5,108,238 A | * | 4/1992 | Ewing .................. F16B 31/021 411/405 |
| 5,490,439 A | | 2/1996 | Matsumura et al. |
| 5,562,379 A | | 10/1996 | Rausch et al. |
| 5,582,079 A | * | 12/1996 | Matsumura ........... B25B 21/002 81/56 |
| 5,953,965 A | * | 9/1999 | Kaneyama ............. B25B 21/00 81/469 |
| 6,487,940 B2 | * | 12/2002 | Hart ...................... B25B 21/002 81/55 |
| 7,204,667 B2 | * | 4/2007 | Uno ...................... F16B 31/021 411/338 |
| 7,398,700 B2 | * | 7/2008 | Makimae ............. B23P 19/066 173/176 |
| 2005/0061119 A1 | * | 3/2005 | Becker ................ B25B 23/1425 81/467 |
| 2005/0193869 A1 | * | 9/2005 | Ohtake ................ B25B 21/002 81/57.38 |
| 2007/0144270 A1 | * | 6/2007 | Crass .................. B25B 23/1425 73/862.21 |
| 2008/0251268 A1 | * | 10/2008 | Kushida ................ B25B 21/00 173/2 |
| 2009/0114067 A1 | * | 5/2009 | Berg ...................... B25B 23/15 81/468 |
| 2010/0199782 A1 | * | 8/2010 | Hsieh .................. B25B 23/1425 73/862.23 |
| 2010/0251661 A1 | * | 10/2010 | Illgner .................. F16B 33/004 52/698 |
| 2011/0036206 A1 | | 2/2011 | Yang |
| 2011/0048182 A1 | * | 3/2011 | Goss .................... B25B 13/065 81/478 |
| 2011/0132157 A1 | * | 6/2011 | Duvan ................ B25B 13/462 81/479 |
| 2011/0162493 A1 | * | 7/2011 | Anjanappa ........ B25B 23/1425 81/479 |
| 2011/0271798 A1 | * | 11/2011 | Wagner .................. B25B 29/02 81/57.38 |

FOREIGN PATENT DOCUMENTS

| | | | | |
|---|---|---|---|---|
| DE | 102006044774 A1 | | 4/2008 | |
| GB | 750892 A | * | 6/1956 | .......... B25B 13/463 |
| GB | 750894 A | | 6/1956 | |
| GB | 834787 | | 5/1960 | |
| IT | WO 2008149386 A1 | * | 12/2008 | ............ F16B 33/004 |
| WO | 2008/149386 A1 | | 12/2008 | |

OTHER PUBLICATIONS

"Technical Data Sheet, High Strength Squirter® Assemblies—HSSA" by Cooper & Turner Limited, Construction, Railway and General Engineering Fastenings, from www.cooperandturner.co.uk, 4 pgs, May 2003.

* cited by examiner

TORQUE-ANGLE STRUCTURAL FASTENING SYSTEM

CROSS-REFERENCE TO RELATED APPLICATIONS

This application claims the benefit of priority to U.S. Provisional Patent Application No. 61/466,431, filed on Mar. 22, 2011, the contents of which are incorporated in this application by reference.

STATEMENT REGARDING FEDERALLY SPONSORED RESEARCH

Not applicable

BACKGROUND OF THE INVENTION

The present invention generally relates to fastening systems for assemblies of any two or more components, but particularly useful in commercial structures, utility structures, steel bridges, rail, conveyance, heavy equipment, heavy industrial, construction, agricultural and general structural steel fastening applications.

Structural applications, such as bridges and buildings, typically use welding, bolting, and other means to join at least two components together. Where bolting is used, the process can be quite labor intensive. The process of testing, fitting, bolting and inspecting the connections typically requires at least two laborers, sometimes on opposite sides of the structure or connection. Additional labor for inspection and supplemental equipment operation is often required. The use of more than one laborer requires more safety equipment, project management and oversight, and both direct and indirect labor costs.

Installation requirements of fasteners for these applications are detailed in a number of standards, OEM standards, DOT construction standards and other well-known industry specifications such as those published by the Research Council on Structural Connections (RCSC).

The industry has established at least one dimensional standard for fasteners used in such applications (ASME B18.2.6-2010, which is incorporated by reference herein in its entirety). Other similar standards from different consensus bodies in different markets also exist. Currently, the industry uses a number of different fasteners, including the following:

(a) hex-head and flange head fasteners, which are commonly produced to ASTM A325/A325M, A490/A490M, ASTM A449, ASTM A354, and other standards such as DIN, ISO, JIS, JSS or SAE;

(b) pin-and collar fasteners, which are produced to various consensus and proprietary standards; and (c) twist-off type fasteners, which are produced to ASTM F1852 and F2280, JSS S10T, and other twist off specifications.

Common industry problems among a number of connection types are related to the establishment of two important installation criteria. These two criteria are snug tensioning and final tensioning (often referred to as clamp load). The proper snug tensioning of a given connection, prior to full tensioning, will ensure that all connected plies are in firm and continuous contact, and where application of additional torque or tension to adjacent fasteners will not decrease tension in fasteners already installed. Snug tension should be sufficient to bring plies into continuous contact, or as near continuous contact as possible, but preferably done below the yield strength of the fastener. In connections that require full tensioning, final installation tension can be achieved via a number of methods. Without good control of the snugging operation many fasteners are over tensioned or in some cases connection plies are not brought into firm and continuous contact. In many cases, lubricants are so effective and so little testing is performed on field matched assemblies, that snug tension mistakenly exceeds required final installation tension. Application of further rotation to already highly tensioned fasteners increases the risk of critical failures from fasteners stressed beyond ultimate tensile strength. Severe bolt necking and cracking can result.

Final installation tension is the tension which exceeds minimum design tension to meet the requirement of a particular application, specification or standard. In connections using fastening systems subject to final tensioning using torque there are a number of well documented concerns regarding the repeatability and variability of torque based installation methods, including variability in applied torque, changes in environmental conditions, passage of time, equipment repeatability, equipment maintenance, and a number of other potential issues. In connections using fastening systems subject to final tensioning using compression or angle, there are a number of well documented concerns regarding the establishment of a proper snug condition.

Hex-head fasteners are well known in the art and can be installed using conventional air (pneumatic) impact wrenches and other wrenches including hand operated, electrically operated, and hydraulic wrenches. These fasteners are typically installed using either torque-based, compression based or degree-based installation techniques. Existing tool technology cannot perform both snug tensioning and final tensioning tasks adequately or economically with a single tool or in a single operation, from a single side of the connection. Often the final installation of these fasteners requires the use of a reaction arm to apply force against an adjacent fastener or connection member, and the reaction arm can be cumbersome to use and may create clearance and safety problems for the installers. Hex-head fasteners may have complicated washer usage requirements, depending on hole geometry, connection materials, and installation method. Installation of any hex-head fastener may require at least two installers to ensure proper nut rotation relative to the bolt. In some installations, the bolt may shift or "roll" in the hole during installation. For this reason many installation specifications require match marking of bolts and nuts. This operation is often inaccurate, subject to operator or inspector knowledge, and can even be replicated after installation on fasteners which have not been tensioned.

Pin-and-collar fasteners (also known as lock-pin and collar systems) operate on a principle of direct tension. Examples of pin-and-collar fasteners can be found at least in U.S. Pat. Nos. 2,531,048; 3,057,246; 3,915,053; 4,943,196; 5,049,016; and 5,562,379; each of which is incorporated by reference herein in its entirety. Pin-and-collar fasteners have a pin with a first portion with a first plurality of annular rings (as opposed to the helical threads on the bolt of the twist-off fastener), a second portion with a second plurality of annular rings, and a neck portion between the first portion and the second portion. The first portion of the pin is connected to a head of the fastener, and the second portion of the pin defines an end of the fastener. A collar is disposed about the pin for engagement with the first portion. The collar is deformed with coldworking about the pin and the first plurality of annular rings. The pin breaks off at the neck portion when the tensile capacity of the neck portion is exceeded. These fasteners are not removable and the tooling required to install these fasteners is expensive and cumbersome. While these fasteners have a demonstrated capability to fracture in the neck, providing high assurance of direct tensile loads, they have a problem with properly snugging connections, particularly those involving large plies. At a certain point of deformation into the annular rings, the tensile loads begin to be applied against the rings on the pin, not directly to the head bearing surface on the opposite side of the connection. These fasteners are not able to perform efficient, sequential snugging operations.

Twist-off fasteners rely on torque based installation. Examples of twist-off fasteners and related tooling are described in the industry standard specifications ASTM F1852 and F2280, and JSS S10T, which are incorporated by reference herein in their entirety, and at least in GB 834787 A; U.S. Pat. Nos. 2,928,302; 4,637,764; 4,659,267; 4,836,063; and 5,108,238; each of which is incorporated by reference herein in its entirety. These bolts are known by various other names, including TC bolts, Tru-Tension bolts, Tension Control bolts, Torque Control bolts, Tor-Shear bolts and LeJeune bolts, among others. Twist-off fasteners have a bolt with a threaded shank, and a nut in threaded engagement with the threaded shank. The bolt further comprises a head at one end of the shank, and a splined end at the other end of the shank. Importantly, there is a shear groove between the splined end and the threaded shank, causing a stress concentration in that area. A manual wrench or power wrench, which has an inner socket engaged with the splined portion and an outer socket engaged with an outer surface of the nut. The wrench applies a torsional force on the bolt and nut. When the torsional load on the nut exceeds the shear capacity of the shear groove, the splined end is removed from the end of the bolt. In such fastener assemblies, the fastener tensions are related to calculated coefficients of friction, not the actual tensile or clamp load. As such, this fastening system is highly dependent on frictional engagement and the effectiveness of the fastener (in other words, the ability of the fastener to achieve and maintain a desired clamp load) can vary with temperature, lubrication, weathering, and other environmental factors.

It would be desirable to have a fastening system that is capable of achieving a reliable, calibrated and known snug tight condition, with the capability of achieving a desired final clamp load, while being cost-effective, easy to deploy, free from operator error or influence, and capable of easy installation from a single side, by a single installer, with no torque reaction.

BRIEF SUMMARY OF THE INVENTION

The present invention uses a fastener capable of single sided, single operator installation with an installation tool capable of snugging fastener assemblies and connection plies using torque and performing final fastener tensioning using degrees.

The fastener comprises a bolt having a head and a shank extending axially from the head; and a nut. The shank has at least a threaded portion and a splined portion. The splined portion defines one end of the bolt. The threaded portion is positioned at a desired location and length between the head and the splined portion. The inner surface of the nut is in threaded engagement with the threaded portion of the bolt. Unlike the prior art fasteners, there is no groove between the threaded portion and the splined portion.

The tool for installing the fastener comprises a first socket and a second socket, wherein the first socket is engaged with the outer surface of the nut and the second socket is engaged with the splined portion on the fastener, wherein the tool provides at least torque to the fastener. In at least one embodiment, the torque is snugging torque. The tool can also perform final fastener tension, by turning the nut a known number of degrees. The final fastener tension can be done separately without the application of torque, or can be done subsequently to the application of torque. In at least one embodiment, the tool applies both the necessary torque and the desired turn-of-nut angle. In at least one embodiment the tool also allows for removal of the fastener from its installed position.

DETAILED DESCRIPTION OF THE INVENTION

A fastening system comprising a fastener and a tool is presented herein. This system allows for single-sided, single-operator installation using lightweight, non-impacting, ergonomic installation tooling. This invention contemplates a number of embodiments where any one, any combination of some, or all of the embodiments can be incorporated into the fastening system. In addition, this invention contemplates a number of embodiments where any one, any combination of some, or all of the embodiments can be incorporated into a method of using such fastening system.

Figure 1:
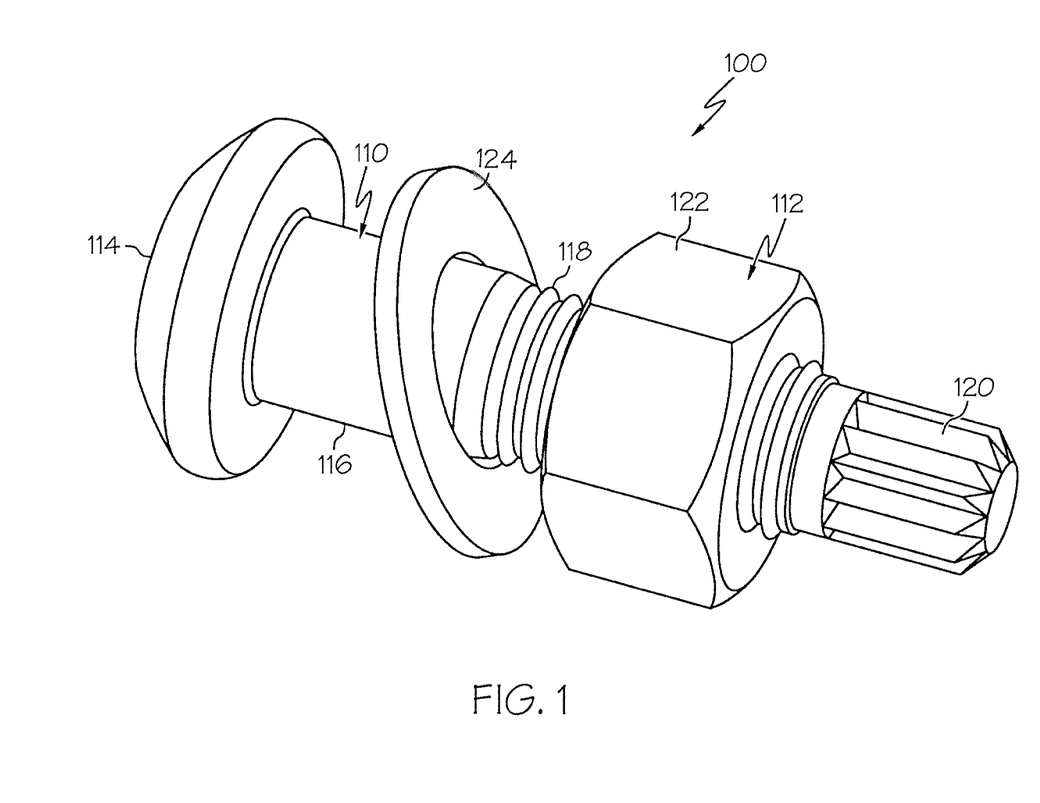
FIG. 1 shows a fastener of the present invention.

FIG. 1 shows an embodiment of a fastener 100 of the present invention, comprising a bolt 110 and a nut 112. The bolt 110 has a head 114 and a cylindrical shank 116 extending axially therefrom. In at least the embodiment shown, the cylindrical shank has a threaded portion 118 and a splined portion 120. The splined portion 120 defines an end of the bolt 110, and the threaded portion 118 is positioned at a desired location between the splined portion 120 and the head 114. The nut 112 can be any suitable nut for the desired application, including standard hex nut, heavy hex nut, hex flange nut locking nut and others. The nut 112 has an outer surface 122 and an inner surface (not shown). The inner surface is threaded to engage with the threaded portion 118 of the bolt 110. In at least one embodiment at least one washer 124 may be used under the nut or head or both to meet the specific application or specification requirements.

Figure 2:
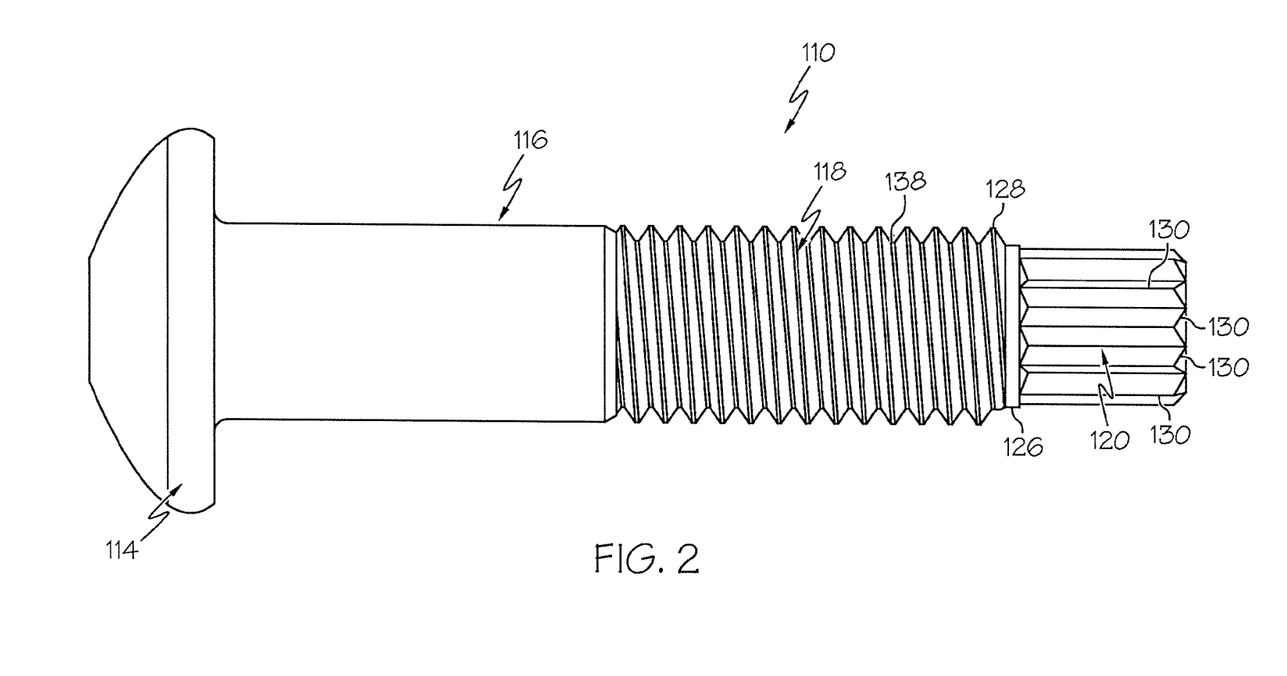
FIG. 2 is a plan view of the bolt of the fastener shown in FIG. 1.

Importantly, as shown in FIG. 2, the connection (shown generally at 126) between the threaded portion 118 and the splined portion 120 does not have a groove, notch or indentation. In the prior art, there is a groove, notch, or indentation between the threaded portion and the splined portion, particularly in twist-off fasteners. This groove or notch creates a relative weakness in the cylindrical shank, where the maximum stress will occur. When the torsional load on the nut exceeds the shear capacity of the groove, the splined portion breaks off from the remainder of the cylindrical shank.

Here, the connection between the threaded portion 118 and the splined portion 120 does not have the groove, notch or indentation. This eliminates the high stress concentration and intentional shearing in that region found in the twist-off fasteners. In various embodiments, the diameter of the splined portion may be greater than, less than or equal to the minor diameter of the threaded portion. In at least one embodiment, the diameter of the splined portion is relative to the minor diameter of the threaded portion. In one embodiment, the diameter can also gradually taper between the threaded portion 118 and the splined portion 120. The threaded portion typically has a major diameter measured at the peaks 128 of the threads, a minor diameter measured at the troughs 138 of the threads, and a pitch diameter dependent upon the pitch or angle of the thread. The major diameter is greater than the pitch diameter, which is greater than the minor diameter. The transition from the threaded portion to the splined portion may vary depending on the application. The threaded portion may have any desired dimensions. The threaded portion may terminate proximate to or at any desired distance from the head 114 along shank 116. In at least one embodiment, there can be multiple threaded portions that are separated along the length of the shank. In at least one embodiment the head portion 114 may be replaced with a heavy hex nut, flange nut or other nut specific to the application.

In the present invention, the connection between the threaded portion 118 and the splined portion 120 is either straight (as shown in FIG. 1) or gradually tapered, and thus will not break off when a desired torsional load has been met, rather it will have the torsional strength to withstand forces applied during torque and angle based installation. Therefore, the splined portion remains after installation, which can be used in the future to uninstall the fastener or to further tension the fastener.

In at least one embodiment, the bolt 110 has a round, rivet-style head, as shown in FIG. 1. In some embodiments, the fastener has a hex-style head or other suitable shaped head. In at least one embodiment, the fastener meets the dimensional requirements of ASTM A325/F1852/A490/F2280, each of which is incorporated by reference herein in their entireties. In at least one embodiment, the fastener meets the nominal dimensions required for the diameter of the shank, the length of the shank, and the thread length of the threaded portion depending upon the application of the fastener.

In at least the embodiment shown, the splined portion 120 has twelve points 130 disposed radially about the shank's circumference. In other embodiments, the splined portion 120 can have any number of points.

In at least one embodiment, the fastener comprises steel. In at least one embodiment, the fastener is manufactured to at least the minimum requirements of ASTM A325/F1852/A490/F2280 in terms of physical, chemical and mechanical properties. In at least one embodiment, the fastener has a tensile strength of at least 120 ksi. In at least one embodiment, the fastener has tensile strength between 120 ksi and 150 ksi. In at least one embodiment, the fastener has a tensile strength of at least 150 ksi.

The fastener of the present invention requires less expense during manufacturing with a nearly scrap free manufacturing process, such as cold forming. The fastener has the appearance of the prior art twist-off (or torsion control) fasteners. However, the present invention is more hardness tolerant, less dependent on lubrication variability, less dependent on washer surface hardness, and less dependent on washer surface roughness. A number of coatings can be used on the fastener with increased performance over the prior art fastener. When bolts are coated there is no need to touch up or recoat the exposed end of the bolt, since it does not shear off, such as with prior art. Also, the present fastener does not require any means for capturing the splined portion or tip that has broken off, making it a safer product, particularly in high-rise or overhead work environments.

Figure 3:
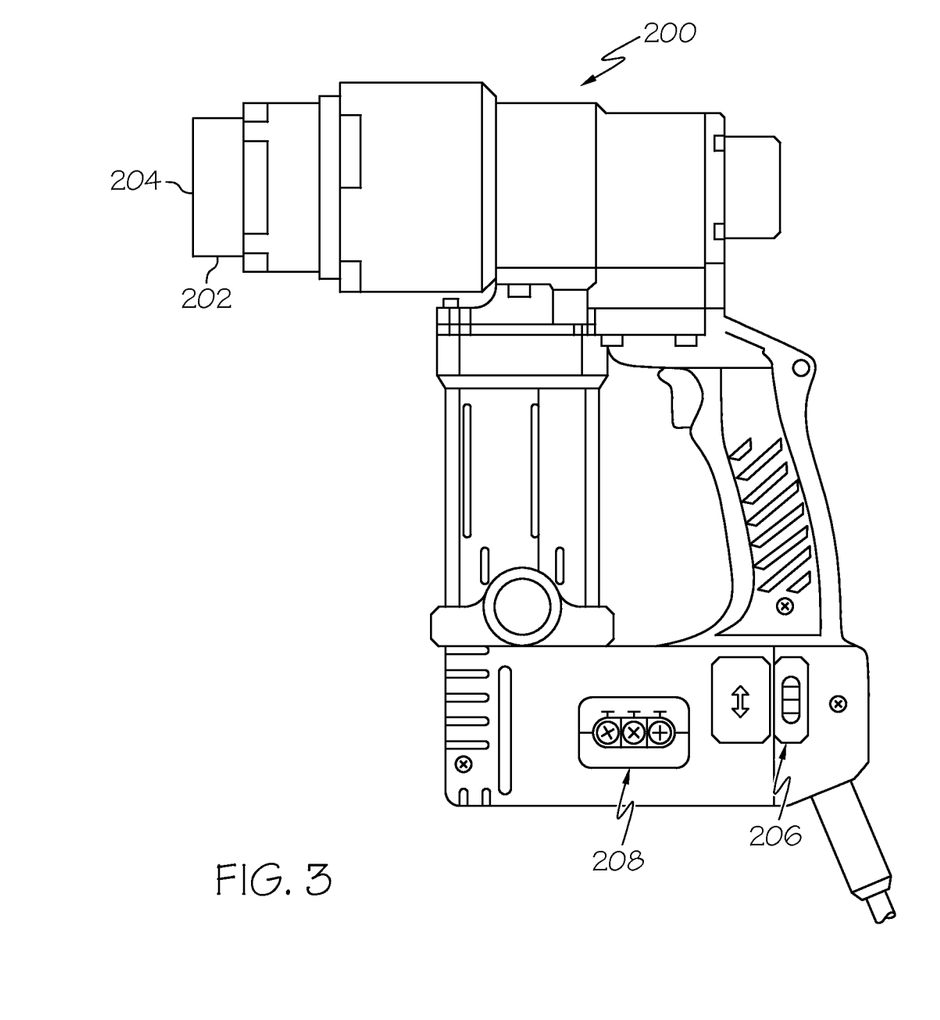
FIG. 3 shows a plan view of the tool of the present invention.

The fastener of the present invention is installed using a tool such as the wrench 200 shown in FIG. 3. The wrench 200 has an outer socket 202 and an inner socket 204. The outer socket 202 engages with the outer surface 122 of the nut 112, and the inner socket 204 engages with the splined portion 120 of the bolt 110. The inner socket 204 counter-rotates relative to the outer socket to install the fastener. In at least one embodiment the same wrench can be used for testing, installation and removal of the fastener 100. Prior art tools for twist off fasteners are one direction (tensioning) only.

In at least one embodiment, rotation of the outer socket 202 relative to rotation of the inner socket 204 allows for the control of snugging torque to keep the fastener in the elastic range of the stress curve during the tightening procedure. "Snugging torque" is a term of art that describes the amount of torque required to bring the workpieces being joined by the fastener (such as all the plies of a steel connection) into firm and continuous or as near continuous as possible contact. This is required to be done before final tensioning in any type of structural steel connection. It is preferred to have the snugging torque at a level below the yield strength of the fastener.

In at least one embodiment, the rotation of the outer socket 202 relative to the rotation of the inner socket 204 provides not only torque, but also turn-of-nut, or angle based tensioning. Unlike previous tools, the application of torque and the final tensioning is accomplished using the same wrench 200. In at least one embodiment, the tool applies torque to the nut and confirms that a desired torque has been reached (meaning the connection and fastener are snug). This snugging operation may need to be done in several sequential operations. Once the tool confirms that the desired torque has been reached, the tool automatically switches or can be switched into final tensioning mode, where the tool rotates the nut a specified number of degrees depending on the application. This is important because when final tensioning is performed on one bolt, the surrounding bolts may lose a small amount of tension due to further compression of the joint. By having a tool that applies both torque and turn-of-nut rotation, all of the fasteners can be uniformly, accurately and reliably loaded, unlike the prior art. As shown in FIG. 3, a switch 206 is provided that an operator can select snugging torque or final tensioning mode.

The tool 200 can have a selectable angle setting 208 between about 10 degrees and 480 degrees, or greater if required. In one embodiment, the tool 200 has an angle setting between about 60 degrees and 480 degrees, or greater if required. In at least one embodiment, the angle setting is provided in increments of 1 degree. In one embodiment, the angle setting is provided in increments of 10 degrees. In one embodiment, the angle setting is provided in increments of 30 degrees. In one embodiment, the angle setting is provided in increments of 60 degrees.

In at least one embodiment, the outer socket and the inner socket rotate in opposite directions at the same rate. In other embodiments, the outer socket and the inner socket may rotate at different rates. It is preferable that the outer socket and the inner socket rotate at the same rate for the ergonomic benefit of the operator. The tool will feel "torque-free" to the operator, and the operator will not have to hold it in place to prevent the tool from "walking" or rotating in one direction of the other.

The inner socket rotates in the second direction (e.g. counter-clockwise) against the outer socket as a means of absorbing torque in the drivetrain of the tool, rather than by the operator or reaction arm. If instead, the inner socket is stationary, the torque applied to the nut would make the tool want to rotate around the fastener or "walk," and the torque would be transferred to the operator. Assuming equal friction, the bolt may want to turn while the nut stayed stationary. The rotation follows the path of least resistance, thus the nut, being typically lubricated, turns clockwise and the bolt remains stationary. Even if the bolt turns slightly that is fine, what is required is nut rotation relative to the bolt, which reaction arm based installations do not guarantee. The number of degrees of turn against the helix angle of the thread provides calculated, well documented, and researched bolt tension.

The wrench used with this fastener has a much lower level of noise or vibration compared to standard impact wrenches. In one embodiment the same tool can be used for multiple diameters. In one embodiment the wrench can be used for turn-of-nut, DTI, or calibrated wrench tensioning. In one embodiment the torque range and degree range can be set for the fastener to be installed. The wrench can be used in torque only mode for connections requiring only snug tight bolts. The wrench can be analog or digital or both. In some embodiments, the wrench can store data that can be transmitted to a computer, either wirelessly or via data card for monitoring and logging for installation quality assurance and record keeping requirements. In some embodiments, the wrench has a visual indicator that confirms final tensioning. The visual indicator may be water soluble or non-water-soluble marking. The visual indicator may also be audible or visual, such as a light indicating full required rotation has been reached. In some embodiments, a user can input the bolt diameter and length, and the tool will automatically set the appropriate torque and rotation. In some embodiments, the user can input the torque and/or number of degrees required for final tensioning. In some embodiments, as described above, the user can incrementally select the desired degrees of turn for final tensioning based on bolt length.

The wrench 200 can be electric-powered, pneumatic-powered, or hydraulic-powered. In at least one embodiment, the wrench is capable of use in spark-free environments.

In at least one embodiment, a lubricant is applied to at least one of the threaded components. The resultant stress of torque applied by the tool at a location between the splined portion and the threaded portion is a function of a torque coefficient of the lubricant, and the resultant stress is below the ultimate stress of the shank at the location of the minor diameter.

Although the present invention describes a splined portion, other alternative means of restraining the shank of the bolt can be used at the end of the shank. For example, a hex recess can be used at the end of the bolt by which the inner socket can engage with the hex recess.

In at least one embodiment, a fastening system comprises a fastener comprising a bolt and a nut, the bolt having a head and a shank extending axially from the head, the shank having at least one threaded portion and at least one splined portion, the splined portion defining an end of the bolt, the threaded portion between the head and the splined portion, the nut having an inner surface and an outer surface, the inner surface in threaded engagement with at least one threaded portion of the bolt; and a tool comprising a first socket and a second socket, wherein the first socket is engaged with the outer surface of the nut and the second socket is engaged with the splined portion of the fastener, wherein the tool provides both a desired snugging torque and a final tensioning to the fastener. In one embodiment, when both the desired snugging torque and the final tensioning are applied to the fastener, the splined portion remains connected to the threaded portion. The first socket rotates in a first direction and the second socket rotates in a second direction opposite the first direction to provide at least one of the desired snugging torque and the final tensioning. In one embodiment, the first socket and the second socket rotate at the same rate. In at least one embodiment, the tool uses turn-of-nut (angle) tensioning to provide the final tensioning to the fastener. In at least one embodiment, the tool comprises an interface where a user can select a desired angle for turn-of-nut tensioning on the tool. In at least one embodiment, the tool comprises an interface where a user can select the desired snugging torque. In one embodiment, the tool comprises a visual indicator of final tensioning. In one embodiment, the splined portion has a diameter and the threaded portion has a minor diameter along the length of the threaded portion, wherein the diameter of the splined portion is relative to the minor diameter of the threaded portion. In some embodiments, the fastener further comprises at least one washer between the bolt and the nut. In some embodiments, the system further comprises a lubricant, wherein the resultant stress of torque applied by the tool at a location between the splined portion and the threaded portion is a function of a torque coefficient of the lubricant, wherein the resultant stress is below the ultimate stress of the shank at the location.

One method of tightening a fastener, which comprises a nut and a bolt, with a single tool with a first socket and a second socket comprises engaging the first socket with an outer surface of the nut; engaging the second socket with the splined portion on the fastener; rotating the first socket relative to the second socket to apply a desired snugging torque; rotating the first socket relative to the second socket to apply final tensioning; wherein the splined portion remains connected to a threaded portion of the fastener. In some embodiments, the method further comprises: selecting on the tool at least one of the desired snugging torque or the angle for final tensioning. In at least one embodiment, the first socket is rotated in a first direction and the second socket is rotated in a second direction opposite the first direction.

In at least one embodiment, a fastener is provided for use with a single tool that provides both a desired snugging torque and a final tensioning torque. The fastener comprises: a bolt having a head and a shank extending axially from the head, the shank having at least one threaded portion and at least one splined portion, the splined portion defining an end of the bolt, at least one threaded portion between the head and the splined portion; and a nut having an inner surface and an outer surface, the inner surface in threaded engagement with the threaded portion of the bolt, wherein the bolt has a torsional strength at a junction between the threaded portion and the splined portion that exceeds both the desired snugging torque and the final tensioning torque. In at least one embodiment, the splined portion has a diameter and the threaded portion has a minor diameter along the length of the threaded portion, wherein the diameter of the splined portion is relative to the minor diameter of the threaded portion. In at least one embodiment, the fastener comprises at least one washer between the bolt and the nut.

The above disclosure is intended to be illustrative and not exhaustive. This description will suggest many variations and alternatives to one of ordinary skill in this art. The various elements shown in the individual figures and described above may be combined or modified for combination as desired. Those skilled in the art may recognize other equivalents to the embodiments described herein, the equivalents of which are intended to be encompassed by the claims attached hereto. All these alternatives and variations are intended to be included within the scope of the claims where the term "comprising" means "including, but not limited to."

The invention claimed is:

1. A fastening system comprising:
a fastener comprising a bolt and a nut, the bolt having a head and a shank extending axially from the head, the shank having at least one threaded portion and at least one splined portion, the splined portion defining an end of the bolt, the threaded portion located between the head and the splined portion, the nut having an inner surface and an outer surface, the inner surface being in threaded engagement with the at least one threaded portion of the bolt; and
a single tool comprising a first socket and a second socket, wherein the first socket is engagable with the outer surface of the nut and the second socket is engagable with the splined portion of the bolt, wherein
the tool is adapted to provide both a desired snugging torque within an elastic range of a stress curve of the fastener and a final tensioning to the fastener, wherein the tool is adapted to rotate the first socket relative to the second socket by a desired turn-of-nut angle to provide the final tensioning to the fastener, and wherein the splined portion remains connected to the threaded portion after final tensioning such that the tool can uninstall or further tension the fastener.

2. The fastening system of claim 1, wherein the first socket rotates in a first direction and the second socket rotates in a second direction opposite the first direction.

3. The fastening system of claim 2, wherein the first socket and the second socket rotate at the same rate.

4. The fastening system of claim 2, wherein the tool comprises an interface where a user can select the desired turn-of-nut angle and/or the desired snugging torque.

5. The fastening system of claim 2, wherein the tool comprises a visual indicator of final tensioning.

6. The fastening system of claim 2, wherein the tool comprises a switch to select one of a snugging torque mode or a final tensioning mode.

7. The fastening system of claim 6, wherein the tool is adapted to automatically switch into the final tensioning mode once the tool confirms that the desired snugging torque has been reached.

8. The fastening system of claim 2, wherein the splined portion has a diameter and the threaded portion has a minor diameter measured at troughs of the threads, and wherein the diameter of the splined portion is less than or equal to the minor diameter of the threaded portion.

9. The fastening system of claim 2, further comprising lubricant applied to at least one of the threaded portion of the bolt and the inner surface of the nut.

10. The fastening system of claim 1 wherein the tool further comprises a selectable angle setting which defines the desired turn-of-nut angle.

11. The fastening system of claim 1 further comprising a connection between the threaded portion and the splined portion which does not have a groove, notch, or indentation, thereby eliminating a high stress concentration at the connection and intentional shearing of the splined portion.

12. A method of tightening a fastener comprising a nut and a bolt with a single tool,
the bolt having a head and a shank extending axially from the head, the shank having at least one threaded portion and at least one splined portion, the splined portion defining an end of the bolt, the threaded portion located between the head and the splined portion, the nut having an inner surface and an outer surface, the inner surface being in threaded engagement with the threaded portion of the bolt,
the single tool comprising a first socket and a second socket, the method comprising:
engaging the first socket with an outer surface of the nut;
engaging the second socket with the splined portion of the bolt;
rotating the first socket relative to the second socket to apply a desired snugging torque within an elastic range of a stress curve of the fastener;
rotating the first socket relative to the second socket to apply final tensioning to the fastener by applying a desired turn-of-nut angle of the nut relative to the bolt,
wherein the splined portion remains connected to the threaded portion of the bolt after final tensioning such that the tool can uninstall or further tension the fastener.

13. The method of claim 12, further comprising selecting on the tool at least one of the desired snugging torque or the desired turn-of-nut angle for final tensioning.

14. The method of claim 12, wherein the first socket is rotated in a first direction and the second socket is rotated in a second direction opposite the first direction.

15. The method of claim 12, wherein the tool confirms that the desired snugging torque has been reached.

16. The method of claim 12, further comprising selecting one of a snugging torque mode or a final tensioning mode.

17. The method of claim 16, wherein the tool automatically switches into the final tensioning mode once the tool confirms that the desired snugging torque has been reached.

18. The method of claim 12, further comprising selecting the desired turn-of-nut angle before rotating the first socket relative to the second socket to apply final tensioning by applying the desired turn-of-nut angle of the nut relative to the bolt.

19. The method of claim 12 wherein the bolt further has a connection between the threaded portion and the splined portion which does not have a groove, notch, or indentation, thereby eliminating a high stress concentration at the connection and intentional shearing of the splined portion.

20. A fastening system comprising:
a fastener comprising a bolt and a nut, the bolt having a head and a shank extending axially from the head, the shank having at least one threaded portion, at least one splined portion, and a connection between the at least one threaded portion and the at least one splined portion, the at least one splined portion defining an end of the bolt, the at least one threaded portion located between the head and the at least one splined portion, the connection being devoid of a groove, notch, or indentation thereby eliminating a high stress concentration at the connection and intentional shearing of the at least one splined portion, the nut having an inner surface and an outer surface, the inner surface being in threaded engagement with the at least one threaded portion of the bolt; and
a single tool comprising a first socket, a second socket, a selectable angle setting, an indicator of final tensioning, and a switch to select one of a snugging torque mode or a final tensioning mode, wherein the first socket is engagable with the outer surface of the nut and the second socket is engagable with the at least one splined portion of the bolt, wherein
the tool is adapted to provide both a desired snugging torque within an elastic range of a stress curve of the fastener and a final tensioning to the fastener, wherein the tool is adapted to rotate the first socket relative to the second socket by a desired turn-of-nut angle defined by the selectable angle setting to provide the final tensioning to the fastener, and wherein the at least one splined portion remains connected to the at least one threaded portion after final tensioning such that the tool can uninstall or further tension the fastener.

* * * * *